(12) United States Patent
Bockelmann et al.

(10) Patent No.: US 9,499,859 B2
(45) Date of Patent: Nov. 22, 2016

(54) METHOD FOR DETECTING A CIRCULARIZED DNA, AND USE OF SAID METHOD FOR DETECTING MUTATIONS

(75) Inventors: Ulrich Bockelmann, Paris (FR); Virgile Viasnoff, Vanves (FR); Ismaïl Cisse, Aubervilliers (FR)

(73) Assignee: Ulrich Bockelmann, Paris (FR)

( * ) Notice: Subject to any disclaimer, the term of this patent is extended or adjusted under 35 U.S.C. 154(b) by 526 days.

(21) Appl. No.: 13/390,200

(22) PCT Filed: Aug. 13, 2010

(86) PCT No.: PCT/IB2010/053665
§ 371 (c)(1),
(2), (4) Date: May 1, 2012

(87) PCT Pub. No.: WO2011/018774
PCT Pub. Date: Feb. 17, 2011

(65) Prior Publication Data
US 2012/0264630 A1 Oct. 18, 2012

(30) Foreign Application Priority Data
Aug. 13, 2009 (FR) .................................... 09 03950

(51) Int. Cl.
*C12Q 1/68* (2006.01)
*C12P 19/34* (2006.01)

(52) U.S. Cl.
CPC ........... *C12Q 1/6827* (2013.01); *C12Q 1/6853* (2013.01); *C12Q 2525/186* (2013.01)

(58) Field of Classification Search
None
See application file for complete search history.

(56) References Cited

U.S. PATENT DOCUMENTS

| | | | |
|---|---|---|---|
| 5,525,494 A | 6/1996 | Newton | |
| 6,531,302 B1* | 3/2003 | Nerenberg et al. | 435/91.2 |
| 2002/0086289 A1* | 7/2002 | Straus | C12Q 1/6827 435/6.18 |
| 2005/0095606 A1* | 5/2005 | Hoke et al. | 435/6 |
| 2007/0009894 A1* | 1/2007 | Crothers | C12Q 1/6832 435/6.12 |

FOREIGN PATENT DOCUMENTS

| EP | 0 416 817 A2 | 3/1991 |
|---|---|---|
| WO | 99/27137 | 6/1999 |
| WO | 02/24944 A2 | 3/2002 |
| WO | 02/057491 A2 | 7/2002 |
| WO | 2004/057027 A1 | 7/2004 |
| WO | 2006/071770 A2 | 7/2006 |
| WO | 2007/100243 A1 | 9/2007 |

OTHER PUBLICATIONS

Lizardi, Paul M., et al. "Mutation detection and single-molecule counting using isothermal rolling-circle amplification," Jul. 1998, Nature Genetics, 19, pp. 225-232.*
BST DNA Polymerase, Large Fragment FAQ. Datasheet [online]. New England BioLabs Inc., Jan. 23, 2005 [retrieved on Jan. 9, 2013]. Retrieved from the Internet: <URL:http://www.neb.com/nebecomm/products/faqproductM0275.asp>.*
E. coli DNA Ligase. Datasheet [online]. New England BioLabs Inc., Nov. 6, 2011 [retrieved on Jan. 9, 2013]. Retrieved from the Internet: <URL:http://www.neb.com/nebecomm/products/productm0205.asp>.*
Li et al 2009 Clinica Chimica Acta 399: 40-44 (ePub Aug. 23, 2008).*
Banér J., et al., "More Keys to Padlock Probes: Mechanisms for High-Throughput Nucleic Acid Analysis", Feb. 2001, pp. 11-15, Current Opinion in Biotechnology, Feb. 2001, vol. 12, No. 1, XP002575758, ISSN: 0958-1669.
Hausch F., et al., "Multifunctional DNA Conjugates for the In Vitro Section of New Catalysts", Apr. 15, 2000, pp. I-III, Nucleic Acids Research, vol. 28, No. 8, E35, XP002575759, ISSN: 1362-4962.
Zhang, D., et al., "Amplification of Circularizable Probes for the Detection of Target Nucleic Acids and Proteins", Jan. 2006, pp. 61-70, Clinica Chimica Acta; International Journal of Clinical Chemistry, vol. 363, No. 1-2, XP002575757, ISSN: 0009-8981.
Bogard et al., 2005, Techniques de détection des mutations connues, dans Principes de biologie moléculaire en biologie clinique; Paris: Elsevier, p. 720.
Fritz et al., "Translating Biomolecular Recognition into Nanomechanics", Science, vol. 288, Apr. 14, 2000, pp. 316-318.
Hardenbol et al., "Multiplexed genotyping with sequence-tagged molecular inversion probes", Nature Biotechnology, vol. 21, No. 6, Jun. 2003, pp. 673-678.
Farugi et al., "High-throughput genotyping of single nucleotide polymorphisms with rolling circle amplification", BMC Genomics, vol. 2, 2001, 10 pages.
Kim et al., "SNP Genotyping: Technologies and Biomedical Applications", Annual Review of Biomedical Engineering, 2007, pp. 289-320.
Pickering et al., "Integration of DNA ligation and rolling circle amplification for the homogeneous, end-point detection of single nucleotide polymorphisms", Nucleic Acids Research, vol. 30, No. 12, 2002, 7 pages.
Sambrook et al., Molecular Cloning: A Laboratory Manual, 3rd Ed. Cold Spring Harbor Laboratory Press, Cold Spring Harbor, NY, 2001.
Yi et al., "Molecular Zipper: a fluorescent probe for real-time isothermal DNA amplification", Nucleic Acids Research, vol. 34, No. 11, 2006, 5 pages.
Ameziane et al., "Principes de biologie moléculaire en biologie clinique", 2005; Paris : Elsevier, with three pages of English translation of Chapter 12 Summary.
Sambrook et al., "Molecular Cloning: A Laboratory Manual", Third Edition, Cold Spring Harbor Laboratory Press, Cold Spring Harbor, NY, 2001.
Squires et al., "Making it stick: convection, reaction and diffusion in surface-based biosensors", Nature Biotechnology, vol. 26, No. 4, Apr. 2008, pp. 417-426.
Halperin et al., "Brush Effects on DNA Chips: Thermodynamics, Kinetics, and Design Guidelines", Biophysical Journal, vol. 89, Aug. 2005, pp. 796-811.

\* cited by examiner

*Primary Examiner* — David Thomas
(74) *Attorney, Agent, or Firm* — Renner, Otto, Boisselle & Sklar, LLP

(57) ABSTRACT

The present invention relates to a method for detecting a circularized single-stranded DNA by means of the isothermal hyperbranched rolling circle amplification technique, in which the primers used comprise a detectable barcode sequence and, optionally, a spacer which blocks polymerization by DNA polymerase. The present invention also relates to the use of said method for detecting a genetic polymorphism of one or more base pair(s).

12 Claims, 13 Drawing Sheets

Figure 1A:
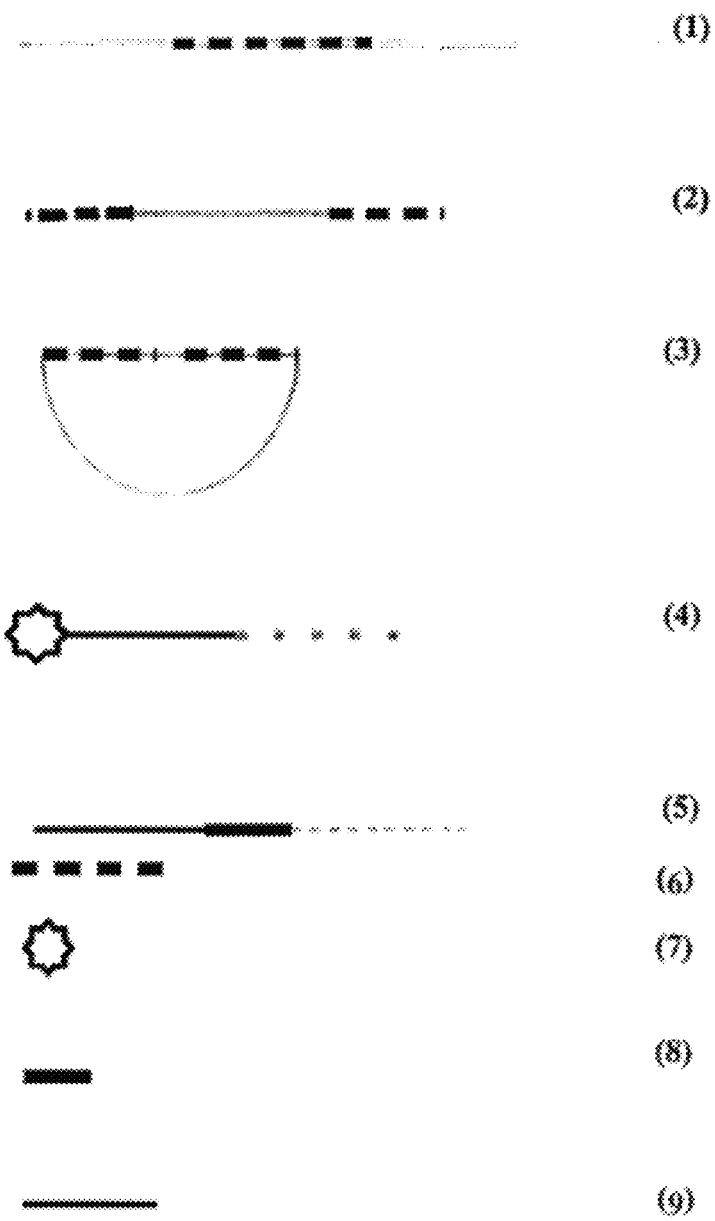
Figure 1:
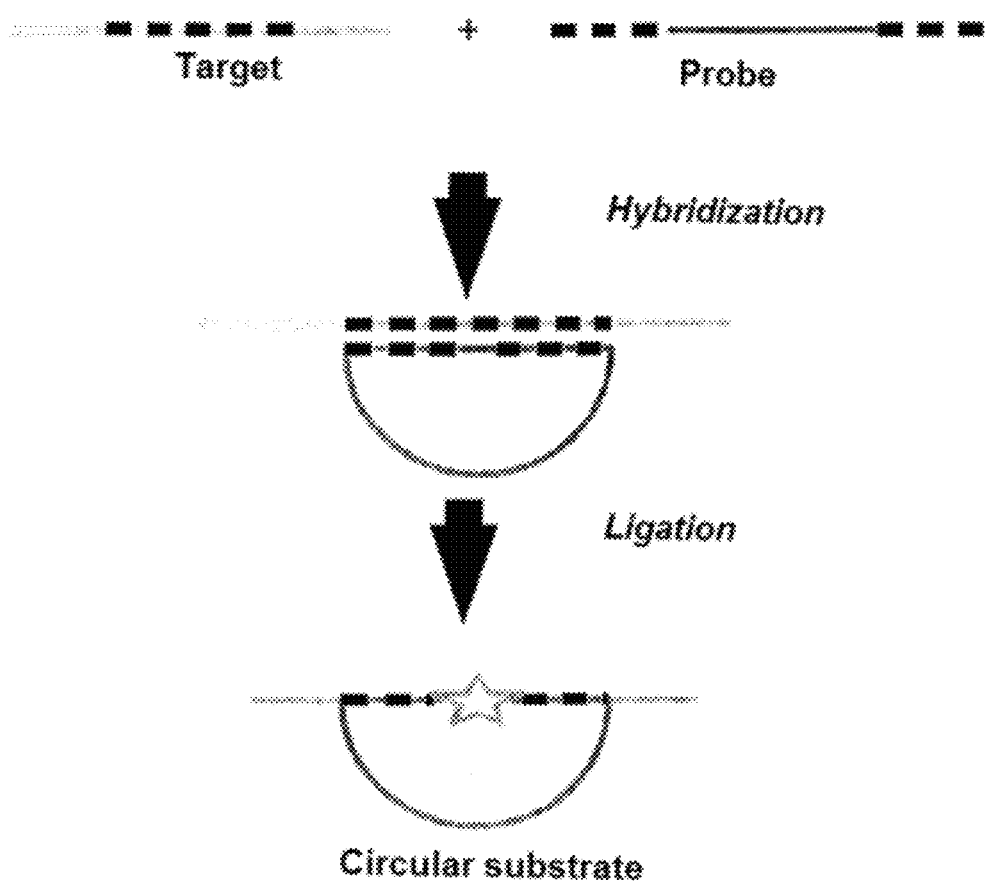

(10)
(11)
(12)
(13)
(14)
(15)
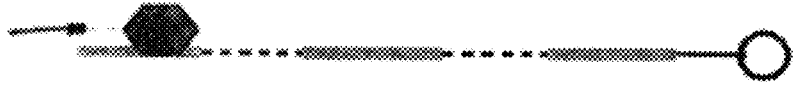
(16)
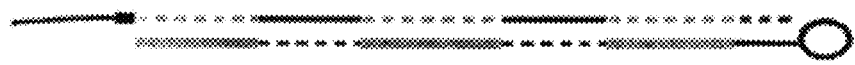
(17)
FIGURE 1 C A
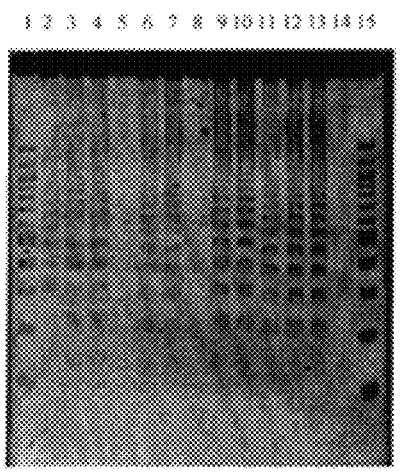
B
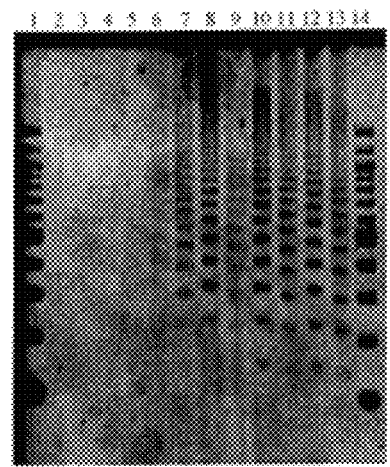
C
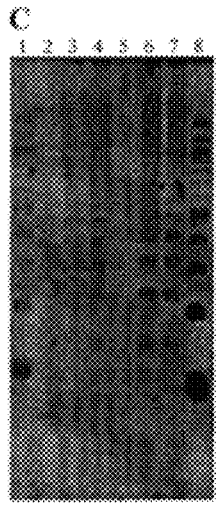
FIGURE 9

SEQUENCE LISTING

```
<160> NUMBER OF SEQ ID NOS: 10

<210> SEQ ID NO 1
<211> LENGTH: 40
<212> TYPE: DNA
<213> ORGANISM: Artificial
<220> FEATURE:
<223> OTHER INFORMATION: Wild type target DNA

<400> SEQUENCE: 1
gctactcgct gaaattaata cgactcacta ggtgccacgg                              40

<210> SEQ ID NO 2
<211> LENGTH: 40
<212> TYPE: DNA
<213> ORGANISM: Artificial
<220> FEATURE:
<223> OTHER INFORMATION: Mutant type target DNA

<400> SEQUENCE: 2
gctactcgct gaaattaata cgaatcacta ggtgccacgg                              40

<210> SEQ ID NO 3
<211> LENGTH: 82
<212> TYPE: DNA
<213> ORGANISM: Artificial
<220> FEATURE:
<223> OTHER INFORMATION: Wild type circularizable nucleotide probe
<220> FEATURE:
<221> NAME/KEY: primer_bind
<222> LOCATION: (25)..(42)
<223> OTHER INFORMATION: Hybridization site for WTFP primer
```

<400> SEQUENCE: 3
tcgtattaat ttcagcgagt gggatcggcg cacctgccgg aaaggccgaa ttcaacggtt    60
gtggtctccc taacctagtg ag                                            82

<210> SEQ ID NO 4
<211> LENGTH: 89
<212> TYPE: DNA
<213> ORGANISM: Artificial
<220> FEATURE:
<223> OTHER INFORMATION: Mutant type circularizable nucleotide probe
<220> FEATURE:
<221> NAME/KEY: primer_bind
<222> LOCATION: (27)..(50)
<223> OTHER INFORMATION: Hybridization site for MutFP primer

<400> SEQUENCE: 4
tcgtattaat ttcagcgagt ttctgactcg tcatgtctca gctctagtac gctgatctta    60
gtgtcaggat acggtgtaga cctagtgat                                     89

<210> SEQ ID NO 5
<211> LENGTH: 38
<212> TYPE: DNA
<213> ORGANISM: Artificial
<220> FEATURE:
<223> OTHER INFORMATION: Wild type forward primer
<220> FEATURE:
<221> NAME/KEY: misc_feature
<222> LOCATION: between (20) and (21)
<223> OTHER INFORMATION: spacer or nothing

<400> SEQUENCE: 5
aacgtcagcc ctgccgcctg ttccggcagg tgcgccga                           38

<210> SEQ ID NO 6
<211> LENGTH: 42
<212> TYPE: DNA
<213> ORGANISM: Artificial
<220> FEATURE:
<223> OTHER INFORMATION: Wild type reverse primer

<400> SEQUENCE: 6
ctaagctgta gccggagtga aggccgaatt caacggttgt gg                      42

<210> SEQ ID NO 7
<211> LENGTH: 46
<212> TYPE: DNA
<213> ORGANISM: Artificial
<220> FEATURE:
<223> OTHER INFORMATION: Mutant type forward primer
<220> FEATURE:
<221> NAME/KEY: misc_feature
<222> LOCATION: between (20) and (21)
<223> OTHER INFORMATION: spacer or nothing

<400> SEQUENCE: 7
ggcggagagt cagttcgcgg gtactagagc tgagacatga cgagtc                  46

<210> SEQ ID NO 8
<211> LENGTH: 44
<212> TYPE: DNA
<213> ORGANISM: Artificial
<220> FEATURE:
<223> OTHER INFORMATION: Mutant type reverse primer

<400> SEQUENCE: 8
ctaagctgta gccggagtga gctgatctta gtgtcaggat acgg                    44

```
<210> SEQ ID NO 9
<211> LENGTH: 20
<212> TYPE: DNA
<213> ORGANISM: Artificial
<220> FEATURE:
<223> OTHER INFORMATION: probe

<400> SEQUENCE: 9
ccgcgaactg actctccgcc                                                 20

<210> SEQ ID NO 10
<211> LENGTH: 20
<212> TYPE: DNA
<213> ORGANISM: Artificial
<220> FEATURE:
<223> OTHER INFORMATION: probe

<400> SEQUENCE: 10
caggcggcag ggctgacgtt                                                 20
```

METHOD FOR DETECTING A CIRCULARIZED DNA, AND USE OF SAID METHOD FOR DETECTING MUTATIONS

The present invention relates to a method for detecting a circularized single-stranded deoxyribonucleic acid (DNA). The invention also relates to the use of this method for the detection of mutations, for example a genetic polymorphism of just one or more base pair(s).

A circularized single-stranded DNA (for example a probe) can be detected using various methods. Some of those methods employ "hyperbranched rolling circle amplification" or HRCA (also known as "ramification amplification" or RAM) (Lizardi et al, 1998, Nature Genetics, 19:225-232).

HRCA is a technique that is used to synthesize branched double-stranded DNA multimers from a circularized single-stranded DNA (substrate) the sequence of which corresponds to the elementary motif (period or monomer) that is to be repeated. That amplification reaction can be carried out at a temperature in the range 37° C. to 70° C., but is generally carried out at a temperature in the range 60° C. to 65° C. in the presence of a DNA polymerase deprived of exonuclease activity and having a strand displacement activity. That DNA polymerase is not only capable, during polymerization of the strand complementary to a DNA matrix (i.e. elongation of a primer hybridized with a DNA matrix), of displacing a strand of DNA hybridized with the DNA matrix that it encounters in order to continue polymerization of the strand complementary to the DNA matrix, but is also deprived of exonuclease activity. Examples of such a DNA polymerase that may be cited are Bst Grand Fragment DNA polymerase (which corresponds to a fragment of DNA polymerase from *Bacillus stearothermophilus*) and DNA Vent exo-polymerase (exo-DNA polymerase from *Thermococcus litoralis*). That amplification process can be used to generate $10^9$ or more copies of the circularized single-stranded DNA in 90 minutes.

Hyperbranched rolling circle amplification of a circularized single-stranded DNA (which may be produced by denaturing a circularized double-stranded DNA, for example) comprises the following steps:

a) hybridizing a first (forward) primer with the circularized single-stranded DNA (termed the negative strand) and polymerization (synthesis) of a periodic single-stranded strand (termed the positive strand), the period of which corresponds to the sequence of the circularized single-stranded DNA, due to the strand displacement activity of the DNA polymerase; the forward primer comprises or is constituted by a nucleotide sequence complementary to a fragment of the circularized single-stranded DNA;

b) hybridizing a second (reverse) primer to each period of the periodic single-stranded strand (positive strand) obtained in step a) and polymerization of a plurality of periodic strands (negative strands) complementary to the positive strand by means of said DNA polymerase that displaces the negative strands hybridized (branched) with the positive strand; the reverse primer comprises or is constituted by a nucleotide sequence identical to a fragment of the circularized single-stranded DNA;

c) hybridizing the first primer to each period of the negative strands obtained in step b) and polymerizing a plurality of periodic strands (positive strands) complementary to the negative strand by means of said DNA polymerase that displaces the positive strands hybridized (branched) with the negative strand;

d) hybridizing the forward and reverse primers respectively to the negative and positive strands generated by polymerization and displacement of the strands;

e) obtaining free or branched periodic double-stranded DNA.

There are currently many methods for detecting a genetic polymorphism (mutation) of a single base pair (SNP) or of a plurality of base pairs (see the review by Kim and Misra, 2007, Annu Rev Biomed Eng, 9:289-320). In order to achieve excellent detection of a genetic polymorphism of a single or of a plurality of base pair(s), a certain number of criteria have to be satisfied:

very good specificity and reliability of the mechanism for recognizing mutations;

good sensitivity in the absence of amplification of genomic DNA prior to detection;

a high degree of multiplexing, i.e. the possibility of screening several thousand mutations and samples in parallel;

low cost per detection and per patient.

The HRCA technique can be employed to detect a genetic polymorphism ((Lizardi et al, cited above; Bogard et al, 2005, Techniques de détection des mutations connues [Known mutation detection techniques], in Principes de biologie moléculaire en biologie clinique; Paris: Elsevier, 720 p). In practice, the target DNA in the single-stranded form (for example a denatured double-stranded genomic DNA) is brought into contact with one or more probe(s) (circularizable single-stranded DNA). If a probe is specific for the target DNA (wild type or mutated), then it hybridizes with its target. After that hybridization step, a step for ligation of the hybridized probe is carried out, generally with the aid of a thermostable DNA ligase (only the probe specifically hybridized to its target being ligated), which causes it to be circularized; that probe is then detected by carrying out the HRCA technique. If a subject is heterozygous for a mutation, then the probes hybridized and circularized respectively to the wild type allele and to the mutated allele can also be detected simultaneously.

Several variations of that technique have been proposed in order to improve the sensitivity and specificity of detection. An example that may be cited is the use of a forward primer or a reverse primer that has a hairpin structure in the 5' position containing a fluorophore and a non-fluorescent quencher (Furaqui et al, 2001, BMC Genomics, 2:4 and Pickering et al, 2002, Nucleic Acids Research, 30:e60), the use of a molecular zipper, which acts as a reverse primer as defined above, and which is in the form of a double-stranded DNA molecule one of the strands of which is conjugated to the fluorescein and the other to a quencher (Yi et al, 2006, Nucleic Acids Research, 34, e81), or the insertion of a tag or barcode and a cleavage site into the nucleotide sequence of the probe (this technique being known as molecular inversion probes, MIP) (Hardenbol et al, 2003, Nature Biotechnology, 21:673-8 and international application WO 02/057491).

However, those techniques are not entirely satisfactory. In fact, detecting a genetic polymorphism using such techniques does not satisfy all of the criteria set out above. Thus, there is a need to improve the HRCA technique in this field.

Within the context of their studies, the inventors sought to improve detection of a genetic polymorphism by the HRCA technique. They thus modified the HRCA technique described by Lizardi et al (cited above) whereby the forward primer is constituted, from its 5' end to its 3' end, by a barcode nucleotide sequence, a linear spacer based on polyethylene glycol (PEG) that can block polymerization by DNA polymerase and a nucleotide sequence that can hybridize with a fragment of a negative strand as described above, and in that the reverse primer is constituted, from its 5' end to its 3' end, by a terminal fluorophore type group, a barcode nucleotide sequence (also termed the binding sequence if that sequence is not detected) and a nucleotide sequence that can hybridize with a fragment of a positive strand as described above.

Carrying out HRCA using these primers means that periodic double-stranded DNA can be obtained, except for the barcode sequence, which remains single-stranded. These periodic double-stranded DNA molecules can then be detected, without being denatured, by hybridization onto a solid support, for example a microarray, supporting nucleotide sequences that are complementary to the barcode sequence as probes. The fact that only the barcode sequence is single-stranded reduces the risks of non-specific interactions and cross-hybridization on the solid support. The inventors have termed this amplification method: "tagged hyperbranched rolling circle amplification" (THRCA). Apart from the primer pairs used, the reaction conditions (pH, buffer, temperature) for THRCA are similar to those of HRCA described by Lizardi et al (cited above).

In order to facilitate comprehension of the invention, amplification by THRCA of a circularized and hybridized probe with a target nucleic acid described above is represented in FIG. 1.

Detection of hybridizing the barcode sequence to said solid support may then be carried out in different manners, for example:

- detection, by fluorescence, either of the fluorophore located at the end opposite to the barcode sequence on the periodic double-stranded DNA, or of tagged dNTPs incorporated into the polymerized DNA strands;
- electronic detection of hybridizing the barcode sequences with a support (for example the active surface of an electronic sensor) as described, for example, in international application WO 2004/057027; the many molecules obtained by THRCA amplification permit good detection of hybridization in that the electrical signal increases with the number of nucleotides that contain the DNA hybridized, via the barcode sequence, with the active surface of an electronic sensor; or
- any other technique for detection by hybridization in which the signal for detecting hybridization between the barcode sequence and a nucleotide sequence (probe) complementary to said barcode sequence increases with the number of nucleotides of the nucleic acid molecule comprising said barcode sequence at its end.

In a variation of the THRCA, the primers do not include a spacer. In this case, before the step for detecting the barcode sequences, the double-stranded periodic DNA may be incubated with an exonuclease or a restriction enzyme in order to obtain double-stranded periodic DNA with a single-stranded barcode sequence.

As a consequence, the present invention provides a method for detecting a circularized single-stranded DNA by hyperbranched rolling circle amplification (HRCA) of said circularized single-stranded DNA in the presence of a forward primer that is capable of hybridizing with said circularized single-stranded DNA and with negative strands generated during the HRCA, and a reverse primer that is capable of hybridizing with positive strands generated during the HRCA, said HRCA generating periodic double-stranded DNAs, said method being characterized in that:

said forward primer is constituted by or comprises the following sequence, from its 5' end to its 3' end: 5'-(F1)$_{n1}$-T1-(E1)$_{m1}$-A1-3', in which:
- F1 represents a terminal group selected from a tag and a coupling agent;
- T1 represents a barcode nucleotide sequence, preferably constituted by 6 to 30 nucleotides, preferably 10 to 25 nucleotides;
- E1 represents a spacer that blocks polymerization of the strand complementary to said nucleotide sequence T1 by a DNA polymerase deprived of exonuclease activity and having a strand displacement activity;
- A1 represents a nucleotide sequence, preferably constituted by 10 to 40 nucleotides, preferably 15 to 25 nucleotides, that is capable of hybridizing with said circularized single-stranded DNA and with said negative strands; as a consequence, the nucleotide sequence of A1 is complementary to a fragment of said circularized single-stranded DNA; and
- n1 and m1 are independently a whole number equal to 0 or 1; preferably, n1=0 and m1=1;

and/or said reverse primer is constituted by or comprises the following sequence, from its 5' end to its 3' end: 5'-(F2)$_{n2}$-T2-(E2)$_{m2}$-A2-3', in which:
- F2 represents a terminal group selected from a tag and a coupling agent, which may be identical to or different from the terminal group F1;
- T2 represents a barcode nucleotide sequence, preferably constituted by 6 to 30 nucleotides, preferably 10 to 25 nucleotides, which may be identical to or different from the nucleotide sequence T1;
- E2 represents a spacer that blocks polymerization of the strand complementary to said nucleotide sequence T2 by a DNA polymerase deprived of exonuclease activity and having a strand displacement activity;
- A2 represents a nucleotide sequence, preferably constituted by 10 to 40 nucleotides, preferably 15 to 25 nucleotides, that is capable of hybridizing with said positive strands; as a consequence, the nucleotide sequence of A2 is identical to a fragment of said circularized single-stranded DNA; and
- n2 and m2 are independently a whole number equal to 0 or 1; preferably, n2=1 and m2=0;

said circularized single-stranded DNA being detected by hybridizing said barcode sequences T1 and/or T2 present at the ends of said double-stranded periodic DNAs with a nucleotide probe complementary to said barcode sequences T1 and/or T2.

When a forward primer with sequence 5'-(F1)$_{n1}$-T1-(E1)$_{m1}$-A1-3' or a reverse primer with sequence 5'-(F2)$_{n2}$-T2-(E2)$_{m2}$-A2-3' as defined above is used to carry out the detection method of the present invention, then the other primer (respectively anti-sense or forward) is any type of primer that can be used in the context of hyperbranched rolling circle amplification.

Hyperbranched rolling circle amplification using the primers as defined above will hereinafter be termed THRCA (tagged hyperbranched rolling circle amplification). THRCA is carried out at a temperature in the range 37° C. to 70° C., preferably in the range 60° C. to 65° C.

The term "blocking polymerization of the complementary strand" means the fact that a DNA polymerase such as a DNA polymerase deprived of exonuclease activity and having a strand displacement activity does not continue to synthesis (polymerize the strand complementary to the nucleotide sequence T (T1 or T2) when it arrives at the spacer e (E1 or E2) after having synthesized the complementary strand of the nucleotide sequence A (A1 or A2). Providing evidence of the function of blocking polymerization during THRCA by a spacer can be carried out in accordance with Example 1 below (see paragraph 1-2-a).

In accordance with a preferred implementation of the invention, the DNA polymerase deprived of exonuclease activity and having a strand displacement activity is the Bst Grand Fragment DNA polymerase or the Vent exo-DNA polymerase.

In accordance with another preferred implementation of the invention, m1+m2 is equal to 1 or 2; i.e. one or both primers comprise a spacer.

The spacer E1 and/or E2 is preferably selected from the group constituted by an abasic site and a linear or branched, optionally substituted alkyl, alkenyl or alkynyl group. Such spacers are well known to the skilled person (see, for example, patent application EP 0 416 817).

Advantageous examples of spacers that may be cited are spacers constituted by or comprising a polyethylene glycol, constituted by a concatenation of 1 to 100, preferably 1 to 50, more preferably 2 to 10, still more preferably 4 to 8 and even more preferably 6 ethylene glycol units, and a $PO_4$ group at one of their ends.

Preferably, the spacer E1 and/or E2 has the following formula I:

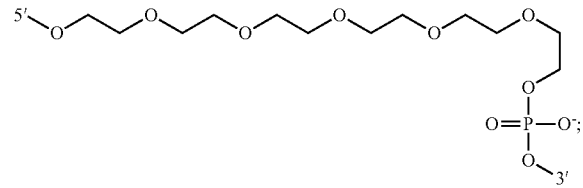

with the 5' to 3' numbering in formula I indicating that the "5' end" of the spacer is bonded to the 3' end of the T sequence (T1 or T2) and that the "3' end" is bonded to the 5' end of the sequence A (A1 or A2).

Methods for synthesizing oligonucleotides comprising a spacer as defined above are well known to the skilled person.

In accordance with one advantageous implementation of the invention, the sequences T1, A1, T2 and A2 do not hybridize with each other under the THRCA reaction conditions.

The terminal group is a compound coupled to the 5' end of the barcode sequence T (T1 or T2), which may be a tag used to detect the DNA, or a coupling agent. It is preferably selected from the group constituted by:
 a luminescent agent, such as radioluminescent, chemoluminescent, fluorescent (for example Cy3 and Cy5) or phosphorescent agents, or a quantum dot;
 a radioisotope such as $^{32}P$;
 an enzyme such as an enzyme having a chromogenic, fluorigenic or luminescent substrate (for example a peroxidase or an alkaline phosphatase) or enzymes producing or using protons (oxidase or hydrolase);
 an acrylamide group (Li et al, 2009, Clinica Chimica Acta, 399, 40-44);
 biotin;
 a thiol such as a 5'-thiol modifier C6 or a 5'-thiol modifier C6 S—S; and
 a phosphorothioate.

The barcode sequence T (T1 or T2) present in the primers is single-stranded. It is preferably constituted by 10 to 22 nucleotides, more preferably 20 nucleotides. It is not capable of hybridizing with said circularized single-stranded DNA nor with said negative and positive strands under the THRCA reaction conditions. Its sequence may be selected by the skilled person in various manners, in particular using a computer program in order to obtain specific recognition by hybridization (absence of unwanted hybridization between barcode sequences, similar melting points).

The nucleotide sequence A (A1 and A2) is preferably constituted by 20 nucleotides. Its sequence is a function of the sequence of said circularized single-stranded DNA and may be selected by the skilled person in different manners, in particular with the aid of a computer program. The fusion temperatures of A1 and A2 are preferably similar and are advantageously in the range 50° C. to 60° C. inclusive, at a pH in the range 7 to 9 inclusive.

Advantageously, the sequences A1 and A2 are not complementary in order to prevent them from dimerizing.

In accordance with another implementation of the invention, in the case in which m1+m2 is equal to 0 or 1 (i.e. at least one of the two primers does not include a spacer), preferably equal to 0, then before the step for detection of the barcode sequences, said double-stranded periodic DNAs obtained by THRCA may be digested by an enzyme in order to render the barcode sequences single-stranded.

Methods for digestion of a double-stranded DNA by an enzyme in order to obtain a double-stranded DNA wherein one or both ends is/are single-stranded are known to the skilled person. As an example, a double-stranded DNA may be heated and an exonuclease may be used, or a restriction enzyme or a polymerase that recognizes a promoter sequence (Sambrook and Russell, 2001, Molecular Cloning: A Laboratory Manual, 3rd Ed. Cold Spring Harbor Laboratory Press, Cold Spring Harbor, N.Y.). It is also possible to use dideoxyribonucleotides (ddNTP) for polymerization and then to use a restriction enzyme that could only cleave a single strand because of the presence of the ddNTPs.

Advantageously, when an exonuclease is used to obtain a double-stranded DNA with a single-stranded end, then the DNA strands that must not be digested by the exonuclease can be protected by a terminal modification (for example by adding a phosphorothioate) to prevent the exonuclease from reacting with this DNA strand.

Detection of the single-stranded barcode sequence at the end of the double-stranded DNAs obtained using the THRCA technique may be carried out in various manners that are known to the skilled person, for example by detecting its hybridization with a nucleotide sequence (probe) complementary to said barcode sequence, fixed on a solid support, such as a microarray. The methods for detecting a sequence hybridized to a probe fixed on a support are also well known to the skilled person (Sambrook and Russell, 2001, Molecular Cloning: A Laboratory Manual, 3rd Ed. Cold Spring Harbor Laboratory Press, Cold Spring Harbor, N.Y.). It may, for example, be carried out either by detection of the F1 or F2 tag, or by a hybridization detection technique in which the hybridization detection signal between the barcode sequence and the nucleotide sequence (probe) complementary to said barcode sequence increases with the number of nucleotides of the nucleic acid molecule comprising said barcode sequence, such as surface plasmon resonance (for example of the Biacore type), measurement of UV absorption, atomic force microscopy (AFM), detection using mechanical cantilever arrays (Fritz et al, 2000, Science 288, 316-318) or electronic detection using FETs (Field Effect Transistor).

The solid support acting to fix said probe may be a plastic material (for example polystyrene, polycarbonate), or nylon or glass.

Methods for the detection of hybridizing a nucleic acid with a solid support (via a nucleotide probe complementary to said nucleic acid), in which the signal increases as a function of the size of the hybridized molecules, are particularly advantageous in the detection of a single-stranded barcode sequence at the end of double-stranded DNAs obtained by carrying out the THRCA of the present invention. The amplification products obtained are large, which means that they can be readily detected using a hybridization detection technique in which the signal for detection of hybridization between the barcode sequence and a nucleotide sequence (probe) complementary to said barcode sequence increases with the number of nucleotides; an example is an electronic detection method.

Figure 11:
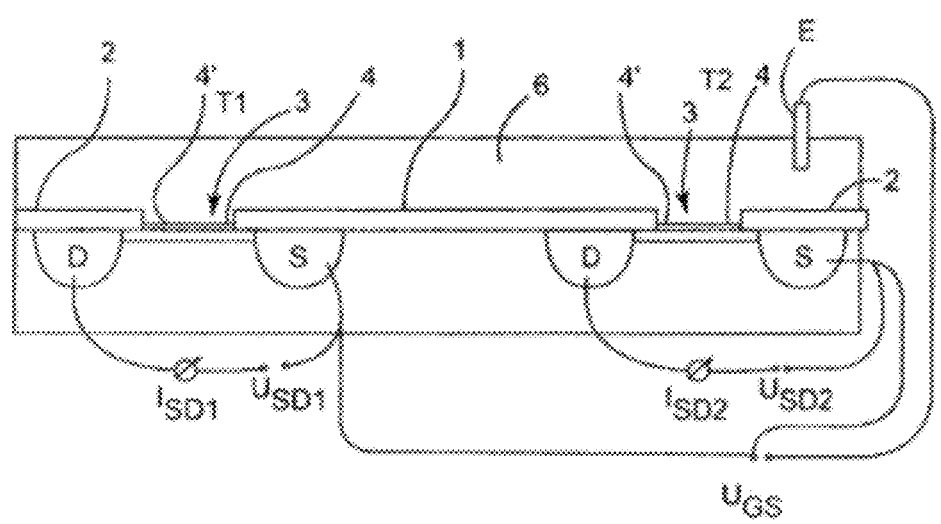

A non-limiting example of a device for carrying out electronic detection that may be cited is a sensor with an array of field effect transistors (FETs) on a silicon substrate. A transistor T1 or T2 represented in section in FIG. 11 is provided with a source region S and a drain region D that each have an electrical contact and are surmounted by an insulating layer, respectively 1 and 2, for example a $SiO_2$ thermal oxide layer. The active region 3 between the source S and the drain D form the gate region G of the transistor and have an insulating layer 4 with a reduced thickness (of 2 nm to 50 nm, preferably 10 nm), for example a layer of thermal $SiO_2$.

A single stranded nucleotide probe (for example DNA) complementary to said barcode nucleotide sequence is fixed, by a method familiar to the skilled person, to at least some of the active surfaces 4. Preferably, n-channel depletion mode field effect transistors are used (for which the charge carriers are electrons, which are more mobile, and hence the detection sensitivity is augmented) with a negative gate polarization (i.e. the electrolyte 6 is negatively polarized with respect to the semiconductor), the probe becoming negatively charged (for an electrolyte with a neutral pH).

Application of a source-drain voltage $U_{SD}$ between the source S and the drain D ($U_{SD1}$ for T1 and $U_{SD2}$ for T2) and a gate-source voltage $U_{GS}$ between the electrolyte 6 and the source S (for example via a single Ag/AgCl electrode E) induces a two-dimensional gas of charge carriers at the Si/$SiO_2$ interface, or at the Si/electrolyte interface of each transistor. This results in a drain current $I_D$ which, for each transistor, depends in a sensitive manner on the charge at the $SiO_2$/electrolyte or Si/electrolyte interface. The term "active surface" is given to this interface which faces the channel between the source S and the drain D.

The current $I_D$ depends on the binding of the probes to the active surface 4.

Detection may be carried out at constant source-gate voltage $U_{SG}$ and source-drain voltage $U_{SD}$, and measuring the drain current $I_{SD}$, or at constant drain current $I_{SD}$ and source-drain voltage $U_{SD}$, and measuring the source-gate voltage $U_{SG}$.

Such a device is described in International patent application WO 2004/057027.

Electronic detection using a sensor (as described above) comprising an array of field effect transistors (T1, T2, etc) each one of which has a source region 5, a drain region D, a gate region that constitutes an active zone 3 on which the specific hybridization between said nucleotide probe and said barcode nucleotide sequence may be detected may comprise the following steps:

a) providing a sensor comprising at least two active zones 3 (see FIG. 11) on which nucleotide probes that are complementary to the barcode sequences are fixed;
b) bringing said nucleotide probes into contact with the amplification product obtained by the THRCA method of the present invention into contact with a reaction buffer having a first concentration of salt in order to obtain a specific hybridization between said nucleotide probes and the barcode sequences; and
c) in a measurement buffer having a second concentration of salt that is lower than that of the reaction buffer, measuring at least one point of the drain current/source-gate voltage/source-drain voltage characteristic of at least one transistor of said array in order to detect said specific hybridization.

Advantageously, the measurement is carried out in a differential manner for probes fixed to distinct active zones 3. In a first variation, this differential measurement is obtained by difference, between the measurement point and a reference point; the measurement point is obtained for nucleotide probes that have been hybridized with a barcode nucleotide sequence (as defined above) in step b) and the reference point is obtained for nucleotide probes that have not been hybridized. In a second variation, the differential measurement is obtained by the difference between two measurement points obtained for probes fixed on distinct active zones 3 that have undergone two different hybridizations, a first specific hybridization with said barcode nucleotide sequence and a second interaction with another nucleotide sequence that is different from said barcode nucleotide sequence.

Figure 2:
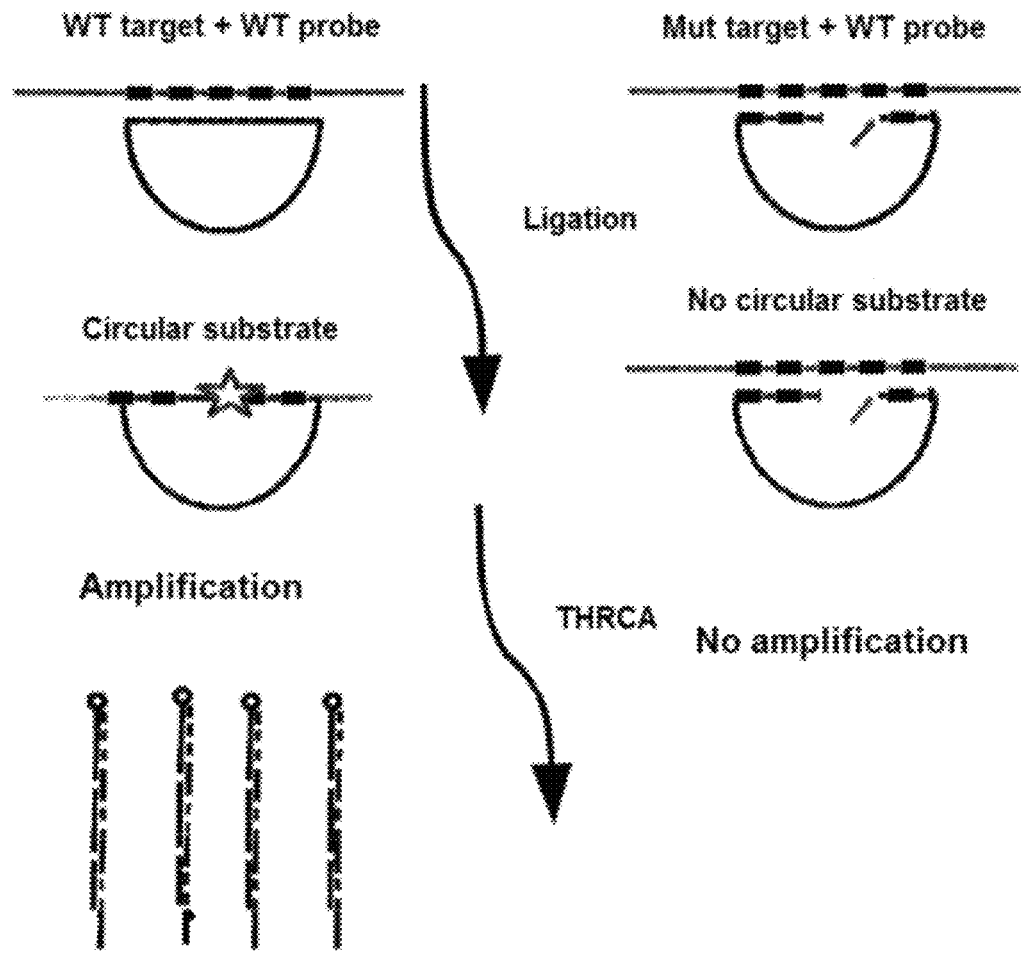

THRCA may be used to detect a genetic polymorphism of a single or of a plurality of base pair(s) (mutations). The principle of detection of a genetic polymorphism by THRCA is represented in FIG. 2. In the case of detection of a genetic polymorphism by multiplexing (detection of a plurality of mutations) and/or in parallel (detection carried out, for example, on different patients using a microarray), then the barcode sequence may be associated with a particular mutation or with a particular patient.

Thus, the present invention also pertains to a method for detecting a genetic polymorphism of a single or of a plurality of base pair(s) (substitution, insertion or deletion of one or more bases), comprising the following steps:

i) bringing a target nucleic acid that might contain one or more polymorphic bases to be detected into contact with a specific circularizable single-stranded DNA (probe) of said polymorphic base or bases;
ii) hybridizing said single-stranded DNA using the target nucleic acid;
iii) if the target nucleic acid contains said polymorphic base or bases, obtaining a hybridized and circularized single-stranded DNA by ligation of said hybridized single-stranded DNA with the target nucleic acid in the presence of a DNA ligase (for example T4 DNA ligase), preferably a thermostable DNA ligase such as AmpDNA ligase (Epicentre Technologies);
iv) obtaining periodic double-stranded DNAs by hyper-branched rolling circle amplification of said hybridized and circularized single-stranded DNA in the presence of at least one of two primers with sequences 5'-$(F1)_{n1}$-T1-$(E1)_{m1}$-A1-3' and 5'-$(F2)_{n2}$-T2-$(E2)_{m2}$-A2-3' as defined above, m1 and m2 preferably being equal to 1 or 2;
v) detecting the barcode sequences T1 and/or T2 present at the ends of the double-stranded periodic DNAs obtained in step iv) by hybridization with a nucleotide probe complementary to said barcode sequences T1 and/or T2 as indicated above; detection of the barcode sequences T1 and/or T2 present at the ends of said periodic double-stranded DNAs indicating that said target nucleic acid contains one or more polymorphic bases.

Clearly, in this implementation of the invention, the nucleotide sequence A1 is not complementary to the fragment of the sequence of said circularized single-stranded DNA that is hybridized with the target nucleic acid.

In step iv), the optimized incubation time for hyperbranched rolling circle amplification may be determined by routine tests carried out by the skilled person. In general, as short a polymerization time as possible is preferred in order to avoid amplification of the linear circularizable probes present, but long enough to obtain said double-stranded periodic DNA in a detectable quantity. Preferably, the incubation time for step iv) is 25 to 90 minutes, more preferably 25 to 35 minutes.

In the context of detection of a genetic polymorphism by multiplexing, i.e. detection of a plurality of mutations (one mutation being defined as one or more polymorphic bases) at a given position on a target DNA, in step i) above the target DNA is brought into contact with a plurality of different circularizable single-stranded DNA molecules (probes): each circularizable single-stranded DNA (probe) molecule is specific to a given mutation at said position. In step iii) above, the circularized single-stranded DNA hybridized to the target nucleic acid is then that which is specific for a given mutation. In step iv) above, several primers with sequences 5'-(F1)$_{n1}$-T1-(E1)$_{m1}$-A1-3' and/or 5'-(F2)$_{n2}$-T2-(E2)$_{m2}$-A2-3' as defined above are used; the nucleotide sequences A1 and A2, and the nucleotide sequences T1 and/or T2 being specific for a given circularizable single-stranded DNA probe. In step v), detection of the barcode sequences T1 and/or T2 present at the ends of the double-stranded periodic DNAs obtained in step iv) indicates that said target nucleic acid contains a given mutation.

The term "target nucleic acid" means a DNA sequence (such as genomic DNA) or single-stranded or double-stranded RNA. Preferably, this target nucleic acid is DNA.

When the target nucleic acid is double-stranded, then a denaturing step may be carried out before step i) in order to put said double-stranded nucleic acid into the single-stranded form.

Before step i), it may also be necessary to fractionate the target nucleic acid by bringing said target nucleic acid into contact with one or more restriction enzymes that are well known to the skilled person. Non-limiting examples of restriction enzymes that may be used are the following enzymes or cocktails of enzymes:

AluI;
DraI et SspI;
EcoR1, Hind111 et BamH1; and
AseI.

In this aspect of the invention, said circularizable single-stranded DNA is also termed a probe. It is constituted by a linear single-stranded DNA sequence of 30 to 140 nucleotides, preferably 50 to 100 nucleotides the ends of which, each of approximately 20 nucleotides, are capable of hybridizing (i.e. are complementary) with contiguous fragments of the target nucleic acid, such that the 5' and 3' ends of said single-stranded DNA are adjacent. When the ends of said single-stranded DNA are hybridized with the target nucleic acid, then they may be bonded together by a DNA ligase to form a circularized single-stranded DNA. The nucleotide sequence between the 5' and 3' ends of the single-stranded DNA contains a fragment complementary to the forward primer as defined above. Such a circularizable single-stranded DNA (probe) is well known to the skilled person.

In accordance with an advantageous implementation of this aspect of the invention, the steps i) to iv) are carried out by mixing said circularizable single-stranded DNA (probe), said single-stranded target nucleic acid, said primers, deoxynucleotides (dNTP), a DNA ligase, rATPs, a DNA polymerase deprived of exonuclease activity and having a strand displacement activity, and a stabilizer for said polymerase (such as bovine serum albumin (BSA) or Triton X-100, in an appropriate buffer in which said DNA ligase circularizes the single-stranded DNA hybridized to the target DNA if hybridization contains no mismatches, and said DNA polymerase catalyzes the polymerization of the DNA strands.

In this implementation, ligation and polymerization are carried out in the same buffer. Thus, it is not necessary to change the reaction medium, to add reagents or to carry out purification of the ligation product in order to permit the THRCA amplification reaction.

Preferably, said buffer comprises or is constituted by potassium acetate, tris-acetate, magnesium acetate and dithiothreitol, preferably at a pH in the range 7 to 9 inclusive, more preferably in the range 7.8 to 8.5 inclusive.

More preferably, said buffer comprises or is constituted by 50 mM of potassium acetate, 20 mM of tris-acetate, 10 mM of magnesium acetate and 1 mM of dithiothreitol, preferably at a pH of 7.9.

In accordance with an advantageous disposition of this implementation, the circularizable probe is ligated at a temperature in the range 1° C. to 37° C., radical in the range 16° C. to 25° C. (temperatures below the amplification temperature).

In accordance with another advantageous disposition of this implementation, said mixture does not contain said DNA polymerase and/or said primers, which are added once ligation of the circularizable probe has been carried out.

The present invention also concerns the use of at least one primer constituted by or comprising the following sequence, from its 5' end to its 3' end: 5'-(F)$_n$-T-E-A-3', in which:

F represents a terminal group as defined above;
T represents a barcode nucleotide sequence, preferably constituted by 6 to 30 nucleotides, preferably 10 to 25 nucleotides, as defined above;
E represents a spacer as defined above that blocks polymerization of the strand complementary to said nucleotide sequence T by a DNA polymerase, preferably a DNA polymerase deprived of exonuclease activity and having a strand displacement activity;
A represents a nucleotide sequence, preferably constituted by 10 to 40 nucleotides, preferably 15 to 25 nucleotides, which can hybridize with a target nucleic acid (or substrate) and initiate polymerization of the strand complementary to said target nucleic acid by said DNA polymerase, preferably a DNA polymerase deprived of exonuclease activity and having a strand displacement activity; and
n is a whole number equal to 0 or 1, preferably 1;

for amplification of a DNA sequence using the PCR technique (for example by multiplex PCR, RAPD-PCR, AS-PCR (allele-specific PCR) or for the detection of a circularized single-stranded DNA by hyperbranched rolling circle amplification or for the detection of a genetic polymorphism of a single or of more base pair(s).

The present invention also pertains to a kit for the detection of a circularized single-stranded DNA or a genetic polymorphism of one or more base pair(s), characterized in that it comprises at least one pair of forward and reverse primers with sequences 5'-(F1)$_{n1}$-T1-(E1)$_{m1}$-A1-3' and 5'-(F2)$_{n2}$-T2-(E2)$_{m2}$-A2-3' as defined above, a DNA ligase, a DNA polymerase deprived of exonuclease activity and having a strand displacement activity, deoxynucleotides, an appropriate buffer, a microarray and, for the detection of a genetic polymorphism, a circularizable single-stranded DNA (probe).

Other aspects and advantages of the present invention will become apparent from the following examples, which should be considered as being by way of non-limiting illustration, and from the accompanying figures in which:

FIG. 1: is a diagrammatic representation of the principle of THRCA: an example with a circularized single-stranded DNA (probe) hybridized with a single-stranded target nucleic acid and a pair of primers of the present invention including a forward primer comprising a spacer but no fluorophore and a reverse primer comprising a fluorophore but no spacer; A: the oligonucleotides employed; (1): single-stranded target nucleic acid (for example genomic DNA); (2): circularizable linear target nucleic acid; (3) circularized single-stranded DNA (probe) (negative strand); (4) reverse primer constituted, from its 5' end to its 3' end, by a fluorophore, a barcode nucleotide sequence (also termed a binding sequence) and a nucleotide sequence identical to a fragment of said probe; (5) forward primer constituted, from its 5' end to its 3' end, by a barcode nucleotide sequence, a spacer and a nucleotide sequence complementary to a fragment of said probe; (6) a zone for hybridizing said probe with the target nucleic acid; (7) fluorophore; (8) spacer; (9) barcode nucleotide sequence; B formation of circular substrate; the star represents the ligase that can ligate the hybridized circularized probe with the target nucleic acid; C amplification by THRCA; (10) hybridization of forward primer with circular substrate (negative strand); (11) polymerization of complementary strand (positive strand) with the probe (the DNA polymerase is represented by a hexagon) (12) when it encounters the target DNA, the polymerase displaces the strand and continues its synthesis (polymerization of strand complementary to the probe); (13) obtaining a periodic single-stranded DNA (positive strand): (14) hybridization of reverse primers with periodic single-stranded DNA and synthesis (polymerization) of complementary strands (negative strands); displacement of synthesized DNA strands will allow the synthesis of periodic single-stranded DNA of different sizes (negative strand); (15): obtaining a plurality of periodic single-stranded strands comprising the barcode sequence (binding sequence) and the fluorophore at one of their ends; (16): hybridizing the forward primer with the periodic single-stranded strand and synthesis (polymerization) of the complementary strand; (17): obtaining periodic double-stranded strands tagged with a fluorophore at one of their ends and by a single-stranded barcode sequence at the other end.

FIG. 2: shows the principle of detection of a genetic polymorphism by THRCA. WT target=wild type genomic DNA (for example allele); Mut target=genomic DNA (for example allele) containing a mutation of one or more base pair(s); WT probe: circularizable single-stranded probe that can be circularized and hybridized with said wild type genomic DNA but not to said genomic DNA containing a mutation. The legends are identical to those of FIG. 1.

Figure 3:
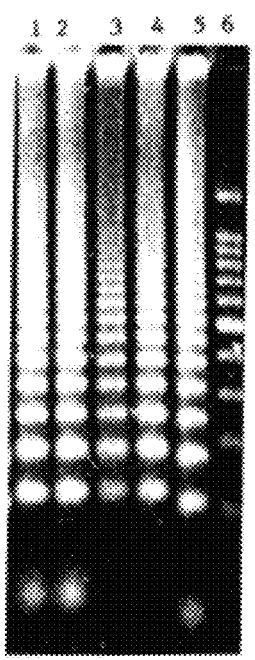

FIG. 3: shows a gel photograph demonstrating blocking of polymerase during THRCA. Wells 1 and 2: products of amplification by THRCA of wild type target DNA substrate/WTCirc probe with the WTFP non-tagged and WTRP tagged with Cy3 primer pair; wells 3 and 4: products of amplification by THRCA of wild type target DNA substrate/WTCirc probe with the WTFP non-tagged and WTRP tagged with Cy5 primer pair; well 5: products of amplification by THRCA of wild type target DNA substrate/WTCirc probe with the WTFP not containing a spacer and non-tagged WTRP primer pair. Well 6: 100 bp NEB molecular weight marker.

Figure 4:
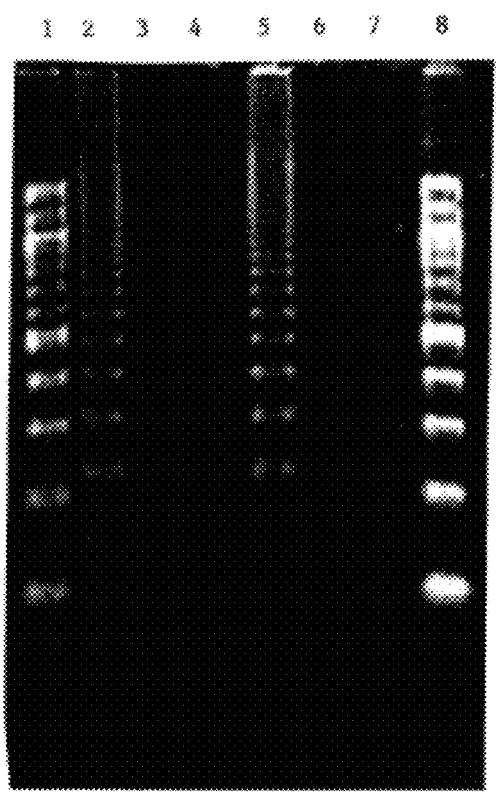

FIG. 4: shows a gel photograph demonstrating the specificity of amplification by THRCA. Wells 1 and 8: 100 bp NEB molecular weight marker. Well 2: amplification product of substrate A (mutant target DNA/MutCirc probe) obtained after 30 min of THRCA reaction; well 3: amplification product of substrate B (mutant target DNA/WTCirc probe) obtained after 30 min of THRCA reaction. Well 4: amplification product of substrate C (wild type target DNA/MutCirc probe) obtained after 30 min of THRCA reaction. Well 5: amplification product of substrate A obtained after 40 min of THRCA reaction. Well 6: amplification product of substrate B obtained after 40 min of THRCA reaction. Well 7: amplification product of substrate C obtained after 40 min of THRCA reaction.

Figure 5:
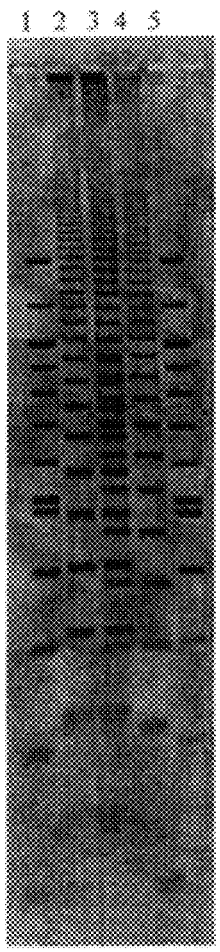

FIG. 5: shows a gel photograph demonstrating amplification by THRCA with multiplexing. Well 1: 100 bp NEB molecular weight marker. Well 2: amplification product of substrate A by THRCA. Well 3: amplification product by THRCA of substrates A (mutant target DNA/MutCirc probe) and D (wild type target DNA/WTCirc probe). Well 4: amplification product by THRCA of substrate D. Well 5: 100 bp NEB molecular weight marker.

Figure 6:
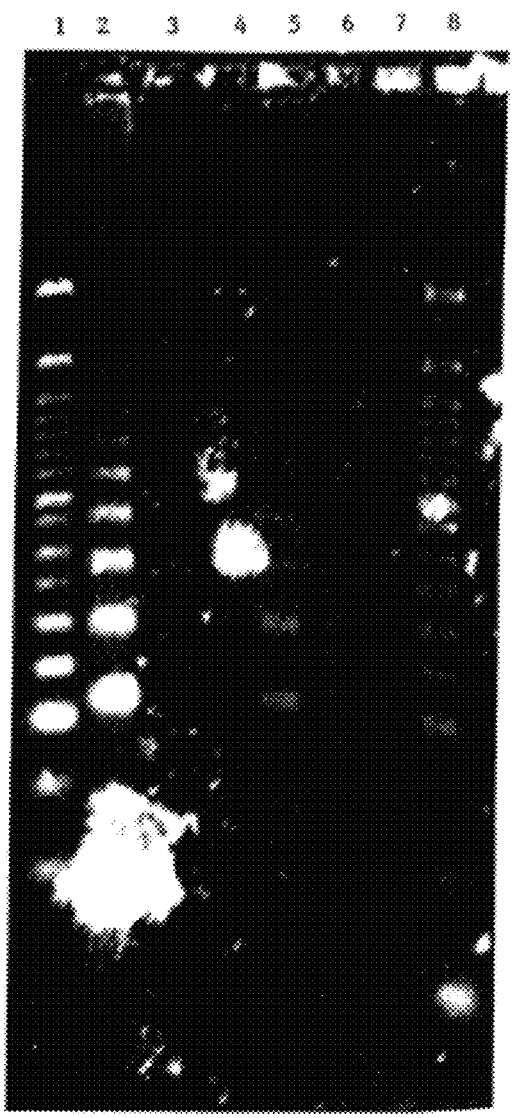

FIG. 6: shows a gel photograph demonstrating the importance of buffer during "one step" THRCA amplification. Wells 1 and 8: 50 bp NEB molecular weight marker. Well 2: amplification product of wild type target DNA substrate/WTCirc probe in modified buffer 4. Well 3: amplification product of Wild type target DNA substrate/WTCirc probe in ligase+BSA type buffer. Well 4: amplification product of wild type target DNA substrate/WTCirc probe in polymerase+rATP buffer. Well 5: amplification product of mutant target DNA substrate/WTCirc probe in modified buffer 4. Well 6: amplification product of mutant target DNA substrate/WTCirc probe in ligase+BSA buffer. Well 7: amplification product of mutant target DNA substrate/WTCirc probe in polymerase+rATP buffer.

Figure 7:
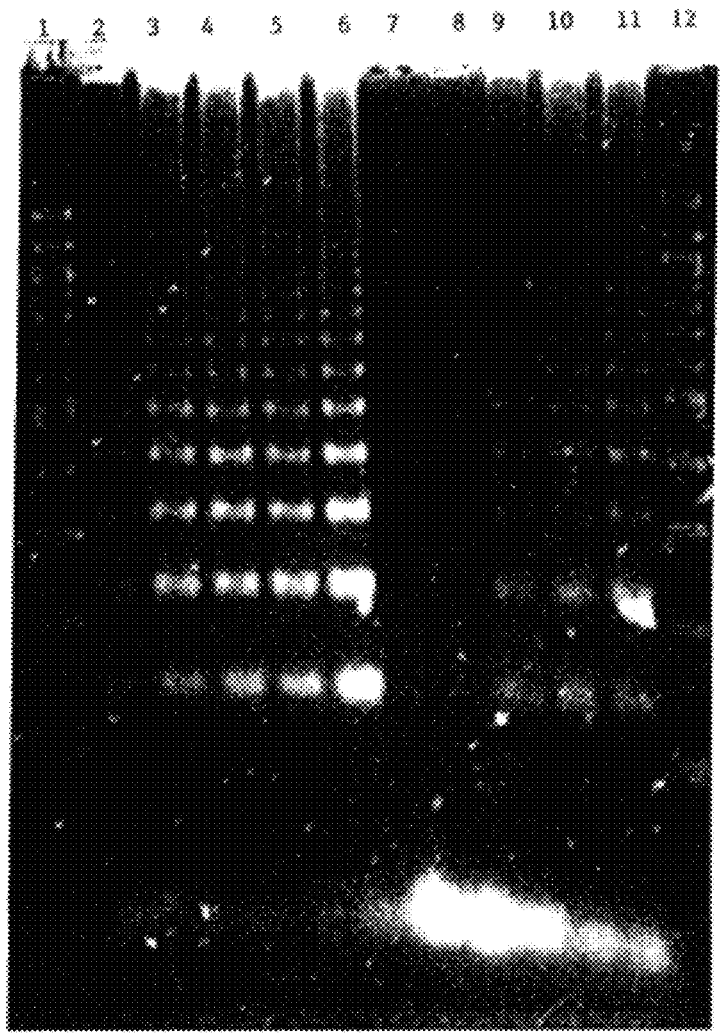

FIG. 7: shows a gel photograph demonstrating the kinetics of the "one step" THRCA amplification reaction. Wells 1 and 12: 100 bp NEB molecular marker. Wells 2 to 6: amplification products of wild type target DNA substrate/WTCirc probe (positive control) respectively obtained after 15 min (well 2), 25 min (well 3), 35 min (well 4), 45 min (well 5) and 50 min (well 6) of reaction. Wells 7 to 11: amplification product of mutant target DNA substrate/WTCirc probe (negative control) respectively after 15 min (well 7), 25 min (well 8), 35 min (well 9), 45 min (well 10) and 50 min (well 11) of reaction.

Figure 8:
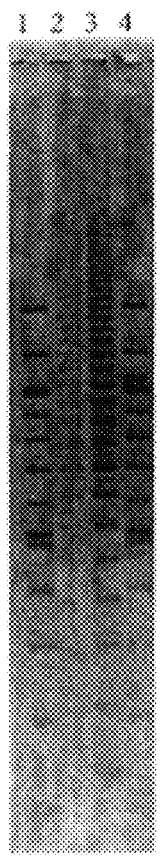
Figure 18:
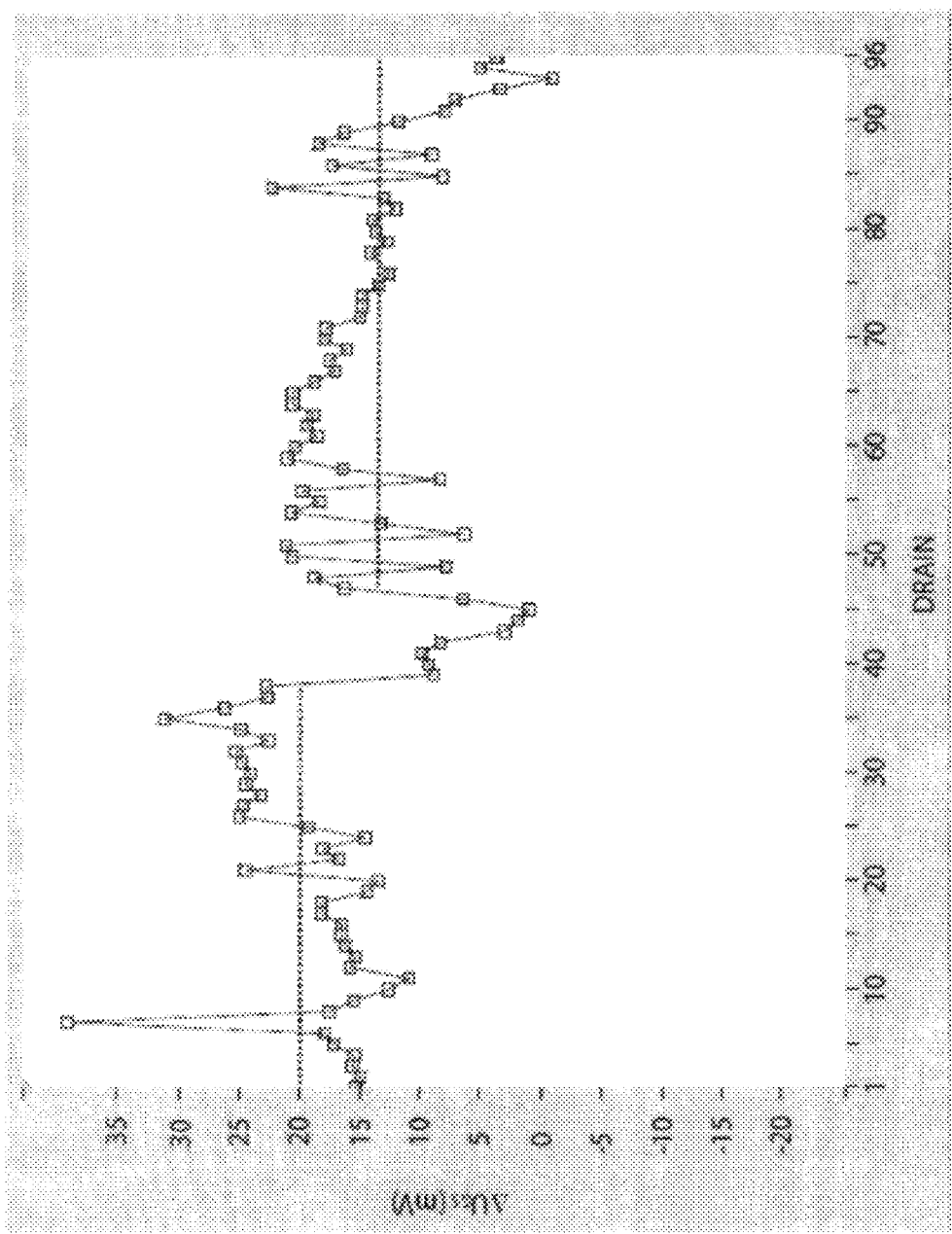

FIG. 8: shows a gel photograph demonstrating blocking of polymerase during THRCA. Wells 1 and 4: 100 bp NEB molecular weight marker. Well 2: amplification product by THRCA of substrate D (wild type target DNA/WTCirc probe) with the WTFP (no spacer)/WTRP (no fluorophore) primer pair. Well 3: amplification product by THRCA of substrate D with the WTFP (with spacer)/WTRP (no fluorophore) primer pair.

FIG. 9: shows a gel photograph demonstrating optimization of amplification time for THRCA. A: wells 1 and 15: 100 bp NEB molecular weight marker. Wells 2, 3 and 4: amplification products of substrate A (mutant target DNA/

MutCirc probe; ligation reaction in presence of ligase) respectively obtained after 30, 60 and 90 min of THRCA reaction. Wells 5, 6 and 7: amplification products of substrate B (mutant target DNA/WTCirc probe; ligation reaction in presence of ligase) respectively obtained after 30, 60 and 90 min of THRCA reaction; wells 8, 9 and 10: amplification products of substrate C (wild type target DNA/MutCirc probe; ligation reaction in presence of ligase) respectively obtained after 30, 60 and 90 min of THRCA reaction; wells 11, 12 and 13: amplification products of substrate D (wild type target DNA/WTCirc probe; ligation reaction in presence of ligase) obtained respectively after 30, 60 and 90 min of reaction THRCA. Well 14: empty. B wells 1 and 14: 100 bp NEB molecular weight marker. Well 2: amplification product of substrate A- (mutant target DNA/MutCirc probe; ligation reaction in absence of ligase) obtained after 30 min of THRCA reaction. Well 3: amplification product of substrate B- (mutant target DNA/WTCirc probe; ligation reaction in the absence of ligase) obtained after 30 min of THRCA reaction. Well 4: amplification product of substrate C- (wild type target DNA/MutCirc probe; ligation reaction in absence of ligase) obtained after 30 min of THRCA reaction. Well 5: amplification product of substrate D- (wild type target DNA/WTCirc probe; ligation reaction in the absence of ligase) obtained after 30 min of THRCA reaction. Wells 6, 7, 8 and 9: amplification products of substrates A-, B-, C- and D-respectively obtained after 60 min of THRCA reaction. Wells 10, 11, 12 and 13: amplification products of substrates A-, B-, C- and D-respectively obtained after 90 min of THRCA reaction. C: wells 1 and 8: 100 bp NEB molecular weight marker. Wells 2, 3 and 4: amplification products of substrate E (WTCirc probe; ligation reaction in the presence of ligase) respectively obtained after 30, 60 and 90 min of THRCA reaction. Wells 5, 6 and 7: amplification products of substrate F (MutCirc probe: ligation reaction in the presence of ligase) respectively obtained after 30, 60 and 90 min of THRCA reaction.

FIG. 10: shows a graph representing the results of the differential electronic measurement between the oligonucleotide probe Ars3 (drains 1-38) and the oligonucleotide probe Ars5 (drains 47-96) after hybridizing the amplification product, by THRCA, of substrate D (wild type target DNA/WTCirc probe) using the following primer pairs: WTFP/WTRP.

FIG. 11: shows a diagram representing two field effect transistors of a detection microarray comprising a plurality of such transistors organized in a one- or two-dimensional array of transistors.

EXAMPLE 1

Carrying Out THRCA 1-1. Materials and Methods
a) Oligonucleotide Sequences
All of the oligonucleotides used had been synthesized by Eurogentec.
Wild Type (WT) DNA Target:

(SEQ ID NO: 1)
5'-GCT ACT CGC TGA AAT TAA TAC GAC TCA CTA GGT

GCC ACG G-3'.

This sequence could, for example, represent a fragment of a wild type allele.

Mutant (Mut) DNA Target:

(SEQ ID NO: 2)
5'-GCT ACT CGC TGA AAT TAA TAC GA<u>A</u> TCA CTA GGT

GCC ACG G-3'.

The sequence of the mutant target DNA differs from the sequence of the wild type target DNA in that the cytosine (C) in position 24 of the sequence for the wild type target DNA has been substituted by an adenine (A). This sequence may, for example, represent a fragment of a mutant allele that would comprise a polymorphism of a single base pair (SNP).
Circularizable wild type probe (single-stranded DNA) (WTCirc):

(SEQ ID NO : 3)
5'[Phos]TCG TAT TAA TTT CAG CGA GTG GGA *TCG GCG*

*CAC CTG CCG* <u>GAA AGG CCG</u> <u>AAT TCA ACG GTT GTG GTC</u>

TCC CTA ACC TAG TGA G-3'.

Circularizable Mutant Probe (Single-Stranded DNA) (MutCirc):

(SEQ ID NO: 4)
5'-[Phos] TCG TAT TAA TTT CAG CGA GTT TCT *GAC*

*TCG TCA TGT CTC AGC TCT AGT AC*<u>G CTG ATC TTA GTG</u>

TCA GGA TAC GGT GTA GAC CTA GTG AT-3'.

The probes comprised a phosphate group (denoted [Phos], $PO_3^{2-}$ in the 5' position in order to allow them to be circularized.
Wild Type Forward Primer (WTFP):

(SEQ ID NO: 5)
5'-AAC GTC AGC CCT GCC GCC TG****TTC CGG CAG GTG

CGC CGA-3'.

**** corresponds to the spacer with formula I:

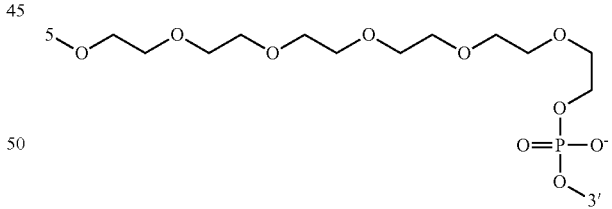

The barcode of the primer is represented by the nucleotide fragment defined by positions 1-20 inclusive. The nucleotide fragment defined by positions 21-38 inclusive is capable of hybridizing with the nucleotide fragment defined by positions 25 to 42 inclusive (in italics) of the WTCirc probe.
Wild Type Reverse Primer (WTRP):
5'-[Cy5/Cy3] CTA AGC TGT AGC CGG AGT G <u>AAGGCCGAATTCAACGGTTGTGG</u>-3' (SEQ ID NO: 6). The WTRP primer was tagged in the 5' position with the fluorophores Cy5 or Cy3. The nucleotide fragment defined by positions 1 to 19 inclusive corresponds to a barcode sequence (termed the binding sequence). The nucleotide fragment defined by positions 20 to 42 inclusive (underlined) is identical to the nucleotide fragment defined by positions 42 to 64 inclusive (underlined) in the WTCirc probe.

Mutant Forward Primer (MutFP):

5'-GGC GGA GAG TCA GTT CGC GG** GTA CTA GAG CTG AGA CAT GAC GAG TC-3' (SEQ ID NO: 7). ** corresponds to the spacer with formula I defined above. The barcode of the primer is represented by the nucleotide fragment defined by positions 1-20 inclusive of the primer MutFP. The nucleotide fragment defined by positions 21-47 inclusive is capable of hybridizing with the nucleotide fragment defined by positions 27 to 50 inclusive (in italics) of the MutCirc probe.

Mutant Reverse Primer (MutRP):

5'-[Cy3] CTA AGC TGT AGC CGG AGT GA GCTGATCTTAGTGTCAGGATACGG-3' (SEQ ID NO: 8). The primer MutRP was tagged in the 5' position with the fluorophore Cy3. The nucleotide fragment defined by positions 1 to 20 inclusive corresponds to a binding sequence. The nucleotide fragment defined by positions 21-44 inclusive (underlined) is identical to the nucleotide fragment defined by positions 51 to 74 inclusive (underlined) of the MutCirc probe.

b) Ligation

The nucleotide probes were mixed with target DNA in order to be circularized by the action of a thermostable ligase: 5 U of Ampligase (Epicentre Technologies) was added to 30 µL of a mixture containing 20 mM of Tris HCl (pH 8.3); 25 mM of KCl; 10 mM of $MgCl_2$; 0.5 mM of NAD; 0.01% of Triton X-100; 300 nM of nucleotide probe and 33 nM of target DNA. The mixture obtained was incubated at 95° C. for 5 min then incubated at 60° C. for 15 min to allow ligation. The products obtained were stored at 4° C.

c) Amplification of Circularized Probes by THRCA

An aliquot of ligation products diluted by 1000 was added to 25 µL of a mixture containing 20 mM of Tris HCl (pH 8.8); 10 mM of KCl; 10 mM of $(NH_4)_2SO_4$; 2 mM of $MgSO_4$; 0.1% of Triton X-100; 200 µM of dNTPs; 1 µM of forward and reverse primers; 2 U of Bst DNA polymerase (NEB). The mixture obtained was incubated at 62° C. for 30 min. 2 µL of the amplification products obtained were then examined by loading them onto 1.5% agarose gel for electrophoresis.

d) "One Step" Amplification by THRCA 60 nM of nucleotide probe and 8 nM of target DNA were added to 30 µL of a mixture containing:

the NEBuffer 4 buffer (NEB, constituted by 20 mM of Tris acetate; 50 mM of potassium acetate; 10 mM of magnesium acetate; 1 mM of dithiothreitol); 100 µg/mL of BSA; 1 mM of rATP (known as "modified buffer 4); or "Ampligase" ligase buffer (Epicentre Technologies); 100 µg/mL of BSA; or "Bst DNA polymerase" polymerase buffer (NEB; note: this buffer contains Triton X-100); 1 mM of rATP; and 200 µM of dNTPs; 1 µM of forward and reverse primers; 2 U of Ampligase (Epicentre Technologies) and 2 U of Bst DNA polymerase (NEB).

The mixture obtained was incubated at 62° C. for 35 min. 2 µL of the amplification products obtained were then examined by loading them onto 1.5% agarose gel for electrophoresis.

1-2. Results a) Demonstration of Blocking of Polymerization During THRCA

Amplification, by THRCA, of the WTCirc probe, circularized and hybridized with the wild type target DNA (termed substrate D) using the primers WTFP (with or without a spacer) and WTRP were carried out. The results are shown in FIG. 3. As can be seen on the gel photograph, there is a difference in the migration between the amplification products obtained using the WTFP primer with a spacer (polymerization blocked) or the WTFP primer without the spacer (polymerization not blocked). When DNA polymerase arrives at the spacer, it encounters the ethylene glycol units forming the spacer and thus cannot continue synthesis. Blocking of the DNA polymerase during synthesis (polymerization) is thus effective with the WTFP primer comprising a spacer.

Further, the presence of fluorophore (Cy3 or Cy5) does not induce a significant difference in migration on the gel. The difference in migration is thus solely due to blocking of polymerization.

The substrate D (wild type target DNA)/WTCirc probe) also underwent amplification by THRCA using either the WTFP (with spacer)/WTRP (without fluorophore) primer pair or the WTFP (without spacer)/WTRP (without fluorophore) primer pair. The results are represented in FIG. 8, which shows the blocking of polymerase when the primer pair WTFP (with spacer)/WTRP (without fluorophore) was used.

b) Specificity of THRCA

When carrying out a clinical test (detection of a genetic polymorphism), it is essential to guarantee the specificity of the amplification obtained by THRCA.

To this end, 3 ligations were carried out:

A: mutant target DNA/MutCirc probe;

B: mutant target DNA/WTCirc probe;

C: wild type target DNA/MutCirc probe.

Substrates A, B and C then underwent amplification by THRCA respectively using the following primer pairs: MutFP/MutRP, WTFP/WTRP and MutFP/MutRP.

The results are shown in FIG. 4. As expected, there was no amplification of products with B or C as substrate, as the probes do not hybridize in their entirety with the target DNA. It could thus be deduced that there was indeed specificity in amplification by THRCA.

c) Amplification by THRCA with Multiplexing

The compatibility of the THRCA method with multiplexing (i.e. several amplification reactions in the same reaction medium) was verified by means of two simultaneous reactions.

To this end, 2 ligations were carried out:

A: mutant target DNA/MutCirc probe;

B: wild type target DNA/WTCirc probe.

Substrates A, D and A+D then underwent amplification by THRCA respectively using the following primer pairs: MutFP/MutRP (for product A), WTFP/WTRP without spacer (for product D) and MutFP/MutRP+WTFP/WTRP (for product A+D).

The results are represented in FIG. 5. It can be seen that for well 3 (THRCA product amplified from substrates A+D), there was an amplification that corresponded to amplification of both A and D at the same time (doubling up of bands).

NB: the offset between the bands of wells 2 and 4 is due to the fact that the probes WTCirc and MutCirc are not the same size and that non-blocking primers (not comprising a spacer) were used in well 4 to accentuate the offset between the bands.

This experiment also shows that it is possible to detect an individual heterozygote for a given gene by carrying out the THRCA technique.

This experiment may be generalized to the detection of several mutations provided that supplemental probes and primers are used.

d) "One Step" Amplification by THRCA

The "one step" method for amplification by THRCA corresponds to an amplification method during which ligation of the probe hybridized with the target DNA and polymerization are carried out in the same reaction medium.

Development of Buffer

The pH of "native" ligase and polymerase buffers are different, and so it was initially necessary to find a single buffer in which the ligase and the polymerase were functional.

Amplification by "one step" THRCA of wild type target DNA substrate/WTCirc or of the mutant target DNA substrate/WTCirc probe (negative control) was tested with 3 different buffers:

i) the buffer NEBuffer 4 (NEB) to which rATPs (necessary for ligase) and BSA (necessary for polymerase) were added (termed "modified buffer 4");

ii) the ligase buffer "Ampligase" sold by Epicentre Technologies, to which BSA (necessary for the polymerase) was added;

iii) the polymerase buffer "Bst DNA polymerase", sold by NEB, to which rATPs (necessary for ligase) were added.

The results are represented in FIG. 6. As can be seen in the gel photograph, only one amplification, in modified buffer 4, was obtained, of the wild type target DNA substrate/WTCirc probe.

However, it should also be noted that the specificity of the reaction was lost, as shown by the amplification of the mutant target DNA substrate/WTCirc probe (negative control). However, it will be noted that the amplification of the negative control was less than the amplification with the positive substrate (wild type target DNA/WTCirc probe). This suggests that there is a temporal window for this specificity.

Kinetics of "One Step" THRCA Amplification Method

It appears from the results described in the preceding paragraph that kinetics is an important factor in guaranteeing the specificity of amplification under these experimental conditions.

Thus, the kinetics of the THRCA reaction starting from wild type target DNA substrate/WTCirc probe (positive control) or mutant target DNA substrate/WTCirc probe (negative control) were studied in modified buffer 4, sampling at t=15 min, t=25 min, t=35 min, t=45 min and t=50 min, taking 2 µL of reaction mixture.

The results are represented in FIG. 7. It appears from the gel photograph that amplification of the (−) products occurred between 25 and 35 minutes after incubation commenced, while that of the (+) products occurred after 15 minutes incubation.

Thus, it can be deduced therefrom that under these experimental conditions, "one step" amplification by THRCA in modified buffer 4 for approximately 30 minutes means that specific amplification of the circularized probe hybridized with the target DNA can be obtained; this is compatible with a clinical application.

e) Determination of Optimal Amplification Time During THRCA Amplification 10 ligations in the presence or absence of ligase, were carried out in accordance with the protocol indicated above (paragraph 1.1-b):

A: mutant target DNA/MutCirc probe (presence of ligase in ligation reaction mixture);

B: mutant target DNA/WTCirc probe (presence of ligase in ligation reaction mixture);

C: wild type target DNA/MutCirc probe (presence of ligase in ligation reaction mixture);

D: wild type target DNA/WTCirc probe (presence of ligase in ligation reaction mixture);

A-: mutant target DNA/MutCirc probe, but ligase not added to ligation reaction mixture;

B-: mutant target DNA/WTCirc probe, but ligase not added to ligation reaction mixture;

C-: wild type target DNA/MutCirc probe, but ligase not added to ligation reaction mixture;

D-: wild type target DNA/WTCirc probe, but ligase not added to ligation reaction mixture;

E (control): WTCirc probe (presence of ligase in ligation reaction mixture);

F (tem): MutCirc probe (presence of ligase in ligation reaction mixture).

The substrates A, B, C, D, A-, B-, C-, D-, E and F then underwent amplification by THRCA for 30, 60 or 90 minutes using the MutFP/MutRP primer pair for substrates A, C, A-, C- and F, and the primer pair WTFP/WTRP for substrates B, D, B-, D- and E.

The results are represented in FIG. 9.

FIG. 9A: as expected, there was amplification of substrates A and D at 30, 60 and 90 min and no amplification of substrates B and C at 30 min. Unexpectedly, there was amplification of substrates B and C at 60 and 90 min.

FIG. 9B: as expected, there was no amplification of substrates A-, B-, C- and D- at 30 min (as ligation could not be carried out in the absence of ligase). Unexpectedly, there was amplification of substrates A-, B-, C- and D- at 60 and 90 min.

FIG. 9C: linear probes are not amplified at 30 min, but they are amplified at 60 and 90 min These results show that the optimal amplification time has to be determined by the skilled person in order to avoid obtaining false positive results.

In the present case, an amplification time of 30 min was optimal. Beyond that time, linear probes were also amplified during THRCA amplification.

EXAMPLE 2

Electronic Detection of Amplification Products Obtained by THRCA

Substrate D as defined above (wild type target DNA/WTCirc probe) underwent amplification by THRCA using the two-step detection protocol (ligation then amplification) using the WTFP/WTRP primer pair.

The THRCA amplification products obtained were then detected using an electronic detection chip comprising an array of field effect transistors as described in International patent application WO 2004/057027 (see also FIG. 11), following substantially the same protocol as that described in Example 1 of that International application.

2.1. Materials

NaOH: 60 mL of 16N NaOH, 420 mL of ethanol and 220 mL of $H_2O$;

$H_2SO_4$, 1M;

PLL: solution of poly-L-lysine, P8920 (Sigma), 0.01% w/v, in PBS 0.1× buffer;

oligonucleotide probe Ars3: 5'-CCG CGA ACT GAC TCT CCG CC-3' (SEQ ID NO: 9), complementary to barcode sequence of MutFP primer (described in Example 1);

oligonucleotide probe Ars5: 5'-CAG GCG GCA GGG CTG ACG TT-3' (SEQ ID NO: 10), complementary to barcode sequence of WTFP primer (described in Example 1).

2.2 Method
General Treatment of Silicon Surface (SiO$_2$) of Field Effect Transistors Incubation for 1 min in sulphuric acid (H$_2$SO$_4$) then rinsing in a stream of deionized water and drying with compressed air. This incubation/rinsing/drying cycle was repeated one more time. Incubation was carried out for 4 min in the NaOH solution followed by rinsing with water and drying.

Electronic Measurement after NaOH Treatment

Measurement buffer: KCl, concentration of 0.01 mM. This measurement was followed by rinsing with water and drying.

General Treatment with Poly-L-Lysine

Incubation with poly-L-lysine for 2 h, then rinsing with water and drying.

Electronic Measurement "PL1"

Measurement buffer: KCl, 0.01 mM. This measurement was followed by rinsing with water and drying.

Electronic Measurement "PL2"

Measurement buffer: KCl, 0.01 mM. This measurement was followed by rinsing with water and drying. This second measurement was intended to check the stability of the measurement at this stage.

Deposition of Oligonucleotide Probes 0.2 µL of a solution containing the oligonucleotide probe Ars3 was deposited, using a micropipette, onto the left hand portion of the array of field effect transistors (drains 1-38). 0.2 µL of a solution containing the oligonucleotide probe Ars5 was deposited on the right hand portion of the array of field effect transistors (drains 47-96). In both cases, the solutions contained 1 µM of oligonucleotide in a 20 mM KCl buffer. Incubation for 15 minutes, in a moist atmosphere, was followed by rinsing with water and drying.

"Probe" Electronic Measurement

The measurement was carried out with a measurement buffer constituted by 0.01 mM KCl, then pumping the electrolyte and replacing with 1 mL of 50 mM KCl, without drying.

Hybridizing THRCA Amplification Product

The buffer was pumped until only 30 µL left. 0.7 µL of THRCA amplification product (1.4 µM) was injected (final dilution of THRCA product was thus of the order of 30 nM). Agitation was carried out by pumping. Deposition and agitation of the THRCA amplification product were carried out a further two times. After agitation, incubation was carried out for 5 min followed by rinsing with 50 mM KCl. This rinse was reiterated 3 times. Next, rinsing was carried out by pumping the electrolyte and 1 mL of 0.01 mM KCl was added, followed by agitation, followed by further pumping. This cycle was reiterated 3 times.

Electronic Measurement after Hybridization

The electrode was immersed in a 0.01 mM KCl buffer and the electronic measurement was carried out.

2.3 Results

The results of the electronic measurement are represented in FIG. 10. The figure shows the differences, deltaUGS, between the electronic measurement "after hybridization" and the "probe" electronic measurement. The mean offset for the "Ars5 region" (drains 47-96) was more negative by 7 mV than that of the "Ars3 region" (drains 1-38). This difference in potential is the signature of hybridization between the oligonucleotide probe Ars5 and the THRCA products carrying the barcode of the primer WTFP.

---

The invention claimed is:

1. A method for detecting a circularized single-stranded DNA comprising the steps of:
   (i) performing hyperbranched rolling circle amplification (HRCA) of said circularized single-stranded DNA in the presence of a forward primer that is capable of hybridizing with said circularized single-stranded DNA and with negative strands generated during the HRCA, and a reverse primer that is capable of hybridizing with positive strands generated during the HRCA, said HRCA generating periodic double-stranded DNAs, wherein:
      said forward primer is constituted by or comprises the following sequence, from its 5' end to its 3' end: 5'-(F1)$_{n1}$-T1-(E1)$_{m1}$-A1-3', in which:
         F1 represents a terminal group selected from a tag and a coupling agent;
         T1 represents a barcode nucleotide sequence constituted by 6 to 30 nucleotides;
         E1 represents a spacer that blocks polymerization of the strand complementary to said nucleotide sequence T1 by a DNA polymerase deprived of exonuclease activity and having a strand displacement activity;
         A1 represents a nucleotide sequence constituted by 10 to 40 nucleotides that is capable of hybridizing with said circularized single-stranded DNA and with said negative strands; and
         n1 and m1 are independently a whole number equal to 0 or 1; and/or
      said reverse primer is constituted by or comprises the following sequence, from its 5' end to its 3' end: 5'-(F2)$_{n2}$-T2-(E2)$_{m2}$-A2-3', in which:
         F2 represents a terminal group selected from a tag and a coupling agent, which may be identical to or different from the terminal group F1;
         T2 represents a barcode nucleotide sequence constituted by 6 to 30 nucleotides, which may be identical to or different from the nucleotide sequence T1;
         E2 represents a spacer that blocks polymerization of the strand complementary to said nucleotide sequence T2 by a DNA polymerase deprived of exonuclease activity and having a strand displacement activity, and which may be identical to or different from the spacer E1;
         A2 represents a nucleotide sequence constituted by 10 to 40 nucleotides that is capable of hybridizing with said positive strands; and
         n2 and m2 are independently a whole number equal to 0 or 1;
      wherein m1+m2 is equal to 1 or 2; and
   (ii) detecting said circularized single-stranded DNA by hybridizing said barcode nucleotide sequences T1 and/or T2 present at the ends of said double-stranded periodic nucleic acids with a nucleotide probe complementary to said barcode sequences T1 and/or T2, said nucleotide probes being present on a solid support.

2. The method as claimed in claim 1, wherein the spacer E1 and/or E2 is selected from the group constituted by an abasic site and a linear or branched, optionally substituted alkyl, alkenyl or alkynyl group.

3. The method as claimed in claim 2, wherein the spacer E1 and/or E2 is constituted by or comprises a polyethylene glycol, constituted by a concatenation of 1 to 100 ethylene glycol units, and by a PO$_3$ group at one of its ends.

4. The method as claimed in claim 3, wherein the spacer E1 and/or E2 has formula I:

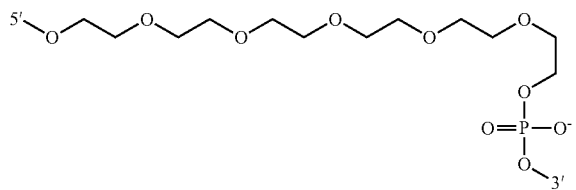

the 5' end of said spacer being bound to the 3' end of said sequence T1 and/or said sequence T2 and the 3' end of said spacer being bound to the 5' end of said sequence A1 and/or said sequence A2.

5. The method as claimed in claim 1, wherein said tag is selected from the group constituted by a luminescent agent, a radioisotope, an enzyme, biotin, acrylamide, a thiol and a phosphorothioate.

6. A method for detecting a genetic polymorphism of a single or of a plurality of base pair(s), comprising the steps of:

i) bringing a target nucleic acid that might contain one or more polymorphic bases to be detected into contact with a circularizable single-stranded DNA probe;
ii) hybridizing said single-stranded DNA using the target nucleic acid;
iii) if the target nucleic acid contains said polymorphic base or bases, obtaining a hybridized and circularized single-stranded DNA by ligation of the ends of said single-stranded DNA by a DNA ligase to form a circularized single-stranded DNA;
iv) obtaining periodic double-stranded DNAs by hyperbranched rolling circle amplification of said hybridized and circularized single-stranded DNA in the presence of at least one of two primers with sequences 5'-(F1)$_{n1}$-T1-(E1)$_{m1}$-A1-3' and 5'-(F2)$_{n2}$-T2-(E2)$_{m2}$-A2-3' as defined in claim 1; and
v) detecting the barcode sequences T1 and/or T2 present at the ends of the double-stranded periodic nucleic acids obtained in step iv) by hybridization with a nucleotide probe complementary to said barcode sequences T1 and/or T2; detection of the barcode sequences T1 and/or T2 present at the ends of said periodic double-stranded DNAs indicating that said target nucleic acid contains said polymorphic base or bases.

7. The method as claimed in claim 6, wherein the steps i) to iv) are carried out by mixing said circularizable single-stranded DNA, said target nucleic acid, said primers, deoxynucleotides, a DNA ligase, rATP, a DNA polymerase deprived of exonuclease activity and having a strand displacement activity, a stabilizer for said polymerase, and an appropriate buffer in which said DNA ligase circularizes the single-stranded DNA hybridized to the target DNA if hybridization contains no mismatches, and said DNA polymerase catalyzes the polymerization of the DNA strands, wherein said appropriate buffer comprises or is constituted by potassium acetate, tris-acetate, magnesium acetate and dithiothreitol.

8. The method as claimed in claim 1, wherein said barcode sequences T1 and/or T2 are detected by a hybridization detection technique in which the detection signal for hybridization between the barcode sequence and a nucleotide sequence probe complementary to said barcode sequence increases with the number of nucleotides of a nucleic acid molecule comprising said barcode sequence.

9. The method as claimed in claim 8, wherein said barcode sequences T1 and/or T2 are detected by an electronic detection method.

10. A kit for detecting a genetic polymorphism of one or more base pair(s), comprising at least one pair of forward and reverse primers with sequences 5'-(F1)$_{n1}$-T1-(E1)$_{m1}$-A1-3' and 5'-(F2)$_{n2}$-T2-(E2)$_{m2}$-A2-3' as defined in claim 1, a circularizable single-stranded DNA, a DNA ligase, a DNA polymerase deprived of exonuclease activity and having a strand displacement activity, deoxynucleotides, an appropriate buffer and a microarray; wherein said appropriate buffer comprises or is constituted by potassium acetate, tris-acetate, magnesium acetate and dithiothreitol.

11. The method as claimed in claim 2, wherein the spacer E1 and/or E2 comprises a polyethylene glycol, constituted by a concatenation of 4 to 8 ethylene glycol units, and by a PO$_3$ group at one of its ends.

12. The method as claimed in claim 11, wherein the spacer E1 and/or E2 has formula I:

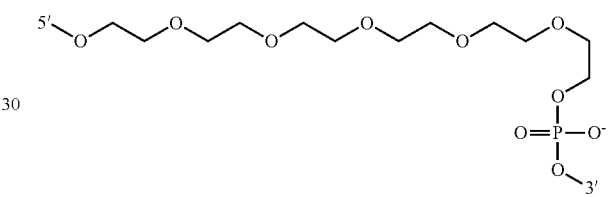

the 5' end of said spacer being bound to the 3' end of said sequence T1 and/or said sequence T2 and the 3' end of said spacer being bound to the 5' end of said sequence A1 and/or said sequence A2.

* * * * *